(12) United States Patent
Al-Otaibi et al.

(10) Patent No.: US 11,692,990 B1
(45) Date of Patent: Jul. 4, 2023

(54) PH MONITORING IN POROUS MEDIA DURING WATERFLOODING EXPERIMENTS

(71) Applicant: SAUDI ARABIAN OIL COMPANY, Dhahran (SA)

(72) Inventors: Mohammed Badri Al-Otaibi, Dhahran (SA); Dong kyu Cha, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 17/648,833

(22) Filed: Jan. 25, 2022

(51) Int. Cl.
| G01N 33/24 | (2006.01) |
| E21B 49/00 | (2006.01) |
| G01N 15/08 | (2006.01) |
| G01N 24/08 | (2006.01) |

(52) U.S. Cl.
CPC ............ *G01N 33/24* (2013.01); *E21B 49/00* (2013.01); *G01N 15/08* (2013.01); *G01N 24/081* (2013.01)

(58) Field of Classification Search
CPC ...... G01N 33/24; G01N 15/08; G01N 24/081; E21B 49/00
See application file for complete search history.

(56) References Cited

U.S. PATENT DOCUMENTS

| 5,945,830 | A | * | 8/1999 | Magowan | ............ | G01N 27/283 324/438 |
| 9,423,367 | B2 | * | 8/2016 | Platte | ...................... | G01N 21/05 |
| 10,480,314 | B2 | | 11/2019 | Ziauddin et al. | | |
| 11,542,812 | B2 | * | 1/2023 | Alghamdi | ............... | G01N 27/60 |
| 2011/0146425 | A1 | * | 6/2011 | Furey | ................... | G01D 11/245 73/866.5 |

(Continued)

FOREIGN PATENT DOCUMENTS

| CN | 209745965 U | * 12/2019 |
| CN | 112924618 A | 6/2021 |
| WO | 2021/130501 A1 | 7/2021 |

OTHER PUBLICATIONS

Advanced Sensor Technologies, Inc., "Rugged Industrial Grade Ion Selective (ISE) Sensors for Continuous Inline, Immersion, Submersible, Sanitary & HOT-TAP Valve Retractable Field Measurements:"; <https://www.astisensor.com/proise.php>; Accessed Sep. 22, 2021 (16 pages).

(Continued)

*Primary Examiner* — Ryan D Walsh
(74) *Attorney, Agent, or Firm* — Osha Bergman Watanabe & Burton LLP (57) ABSTRACT

Provided is a coreflood system that comprises a housing including an inlet end and an outlet end, an inlet positioned at the inlet end, and an outlet positioned at the outlet end. The system includes two chambers positioned within the housing between the inlet and the outlet, configured to retain porous media. The two chambers are in series along a fluid flow pathway through the coreflood system. The system includes a partition extending from an inner surface of the housing between the inlet and the outlet, and a pH sensor provide in a sensor mounting location in the housing having access to the fluid flow pathway. Further provided is a method that comprises directing a fluid into a coreflood system, and using a data processing device coupled to the pH sensor to collect hydrogen ion data and determine hydrogen ion concentration and pH within the fluid.

19 Claims, 5 Drawing Sheets

(56) References Cited

U.S. PATENT DOCUMENTS

2015/0376033 A1\* 12/2015 Tao .......................... C02F 1/44
 210/639
2021/0238998 A1 8/2021 Elsayed et al.

OTHER PUBLICATIONS

Mahzari, P. et al., "Impact of Micro-Dispersion Formation on Effectiveness of Low Salinity Waterflooding"; Proceedings of the IOR 2015—18th European Symposium on Improved Oil Recovery; Apr. 14-16, 2015 (10 pages).

\* cited by examiner

PH MONITORING IN POROUS MEDIA DURING WATERFLOODING EXPERIMENTS

BACKGROUND

In the field of oil and gas, waterflooding is a process to increase production from hydrocarbon-bearing reservoirs. A waterflooding process injects water into a hydrocarbon-producing reservoir. The hydrocarbons within the reservoir are displaced by the water and is pushed toward an adjacent production well. The displaced hydrocarbons are collected and produced.

Waterflooding fluid is often based on a high salinity fluid, such as seawater or brine. Recent research studies have shown that reducing the salinity of water in waterflooding may have a favorable impact on wettability. Wettability of the reservoir rock or mineral is strongly correlated to permeability and general waterflooding behavior. A favorable impact on wettability may result in increased oil recovery.

Coreflooding is a laboratory test that introduces fluid, such as water, into a rock sample to measure interactions between the fluid and the rock. The rock sample used in coreflooding may come from a reservoir, for example, to measure feasibility of a waterflooding process. The lab equipment used for a coreflooding test is a general coreflood apparatus and may be found in in a petroleum research lab.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one aspect, one or more embodiments of the present disclosure may include a coreflood system comprising a housing including an inlet end and an outlet end, an inlet at the inlet end, and an outlet at the outlet end. The system may include two chambers positioned within the housing between the inlet and the outlet, configured to retain porous media. The two chambers may be in series along a fluid flow pathway through the coreflood system. The system may include a partition coupled to an inner surface of the housing and positioned between the inlet and the outlet, a pH sensor provided in sensor mounting location in the housing. The pH sensor may have access to the fluid flow pathway.

In another aspect, one or more embodiments of the present disclosure may include a method, comprising providing a coreflood system that may comprise a housing including an inlet end and an outlet end. The inlet may be positioned at the inlet end. The coreflood system may comprise an outlet coupled to the housing and positioned at the outlet end, and two chambers positioned within the housing between the inlet and the outlet. The two chambers may be in series along a fluid flow pathway through the coreflood system, and the two chambers may prevent fluid bypass around the porous media. The system may include a partition coupled to an inner surface of the housing and positioned between the two chambers, a pH sensor coupled to the sensor mounting location where the pH sensor may have access to the fluid flow pathway. The method may further include providing a porous medium in the two chambers, and directing a fluid through the coreflood system, from the inlet through the fluid flow pathway. The method may further include using a data processing device coupled to the pH sensor to collect hydrogen ion data from the pH sensor and determine a hydrogen ion concentration and pH within the fluid.

Other aspects and advantages of the claimed subject matter will be apparent from the following Detailed Description and the appended Claims.

BRIEF DESCRIPTION OF DRAWINGS

In the figures, a " ' " refers to the same element in a different state, that is, all other aspects of the elements are the same but for a modification in operation. In the figures, like numbers may refer to like elements.

DETAILED DESCRIPTION

In one or more embodiments, a coreflood apparatus has an inlet, an outlet, two or more chambers therebetween, and a partition between each pair of chambers. Such an apparatus may be used to retain samples of porous media, e.g., two or more core samples, in an apparatus—each sample in its own chamber—while fluid may be introduced at the inlet. As fluid flows through porous media, such as core samples, the coreflood apparatus may be used to detect changes in the fluid passing from porous media and therefore determine changes to porous media.

Data collected from a coreflooding experiment using a coreflood apparatus may be useful to analyze damage to the core sample caused by the introduced fluid. For example, analytical data can be useful in determining improvements in a large-scale waterflooding process.

High salinity waterflooding fluids may have high concentrations of ions, such as divalent cations and hydrogen ions, compared to low salinity fluids, like fresh water. In addition, these ions may be present in carbonate rocks and other reservoir rocks. These ions may play a role in interactions between fluid and rock. Hydrogen ions may have a noticeable impact on fluid chemistry through, for example, ionic exchange, mineral dissolution, corrosion, or a combination thereof. Altering the concentration of ions in water may result in rock wettability alteration during waterflooding.

In one or more embodiments, a coreflood apparatus, a coreflood system, and a method of use are provided. One or more embodiments may be used to determine in-situ pH (concentrations of hydrogen ions) during coreflooding.

Determining pH at different positions along the fluid flow pathway of the coreflood apparatus, such as before, between, or after one or more core samples, may help to predict physicochemical interaction between different fluid and rock combinations.

Coreflood Apparatus

Figure 1A:
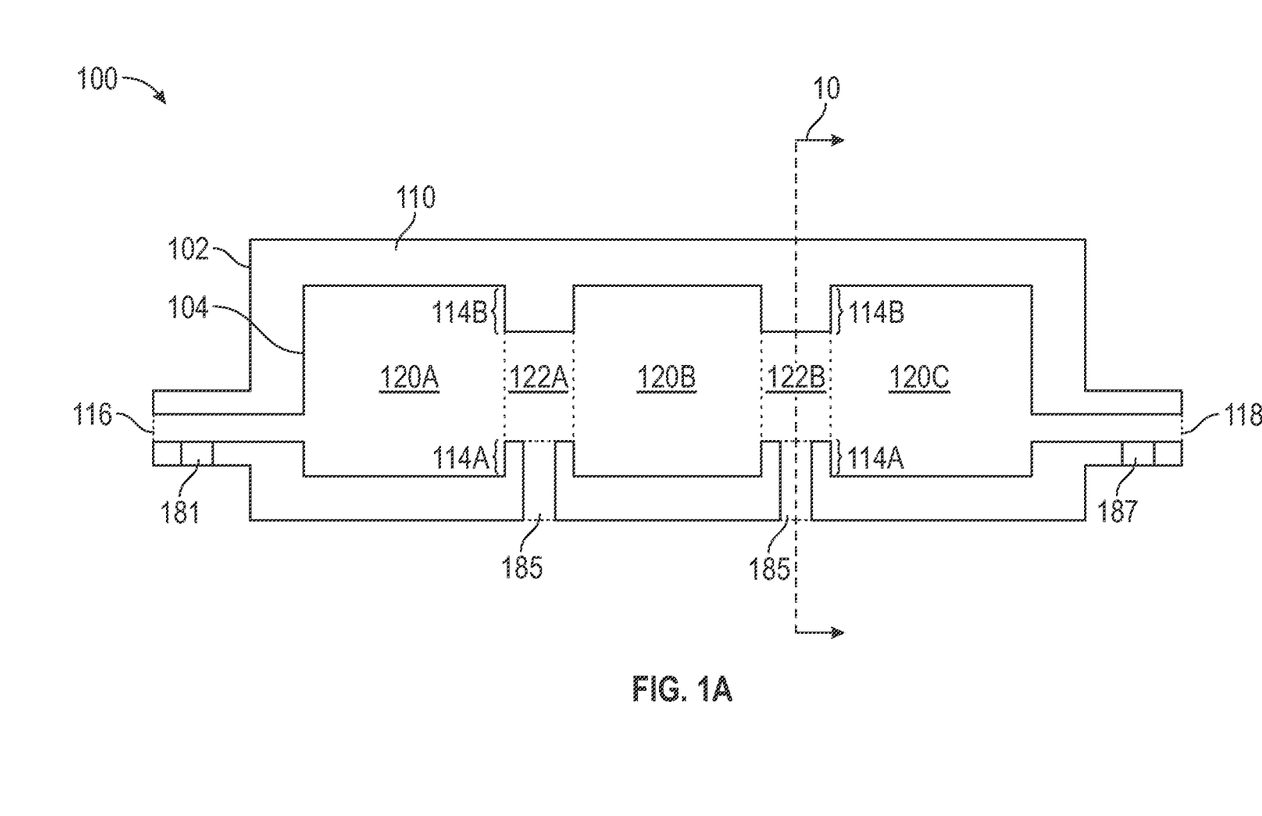
FIG. 1A shows a cross-sectional view of a coreflood apparatus, according to one or more embodiments.

FIG. 1A depicts a cross-sectional view of a coreflood apparatus 100 of one or more embodiments. The cross-sectional view shows the coreflood apparatus 100 and the general fluid flow pathway from inlet end (left) to outlet end (right). The coreflood apparatus 100 includes a housing 110. The housing 110 has an outer surface 102 and an inner surface 104. The inner surface 104 of the housing 110 defines the interior of the coreflood apparatus 100, including the chambers. FIG. 1A shows inlet chamber 120A, middle chamber 120B, and outlet chamber 120C. An inlet 116 is defined by the housing 110 at the inlet end, and an outlet 118 is defined by the housing 110 at the outlet end. The coreflood apparatus 100 is configured such that a fluid may be introduced through the inlet 116, traverse the interior of the housing 110, and pass from the outlet 118.

The inner surface 104 defines an open space within the housing 110. Between the inlet 116 and the outlet 118, a plurality of chambers is defined within the housing 110. In FIG. 1A, three chambers are shown. Inlet chamber 120A, middle chamber 120B, and outlet chamber 120C are in series and in fluid communication with one another along the fluid flow pathway. The inlet 116 is configured to pass fluid to the inlet chamber 120A. The outlet 118 is configured to receive fluid from the outlet chamber 120C.

The inner surface 104 also defines partitions within the housing. A partition is positioned between two chambers in series (each of two chambers) and in part defines the configuration of a chamber and a partition gap. For example, there is a partition positioned in between inlet chamber 120A and middle chamber 120B, which defines a partition gap 122A. There is another partition positioned in between middle chamber 120B and outlet chamber 120C, forming a partition gap 122B. A partition is configured to separate the chambers. Thus, the partition defines both a part of each chamber and a partition gap that exists between and is in fluid connectivity with each chamber.

As shown in FIG. 1A, the partition may have two parts: a portion of the partition with a sensor mounting location 114A and another portion of the partition without sensor mounting location 114B.

The configuration of the housing of the coreflood apparatus provides for at least one partition having a sensor mounting location. The sensor mounting location may define access through the housing for a pH sensor and permit detection of hydrogen ions in a fluid flowing through the coreflood apparatus with the pH sensor. Meaning, the configuration of the partition with the sensor mounting location may define an orifice or void, such as a hole or a conduit, to house a sensor, to be described. For example, the sensor mounting location may include threads, a poppet, a grommet, a clamp, an O-ring, or other suitable configuration to retain a sensor. When a sensor is not included at the sensor mounting location, the sensor mounting location may be blocked off to prevent fluid loss or gas exchange, for example, blocked off with a plug.

The housing of the coreflood apparatus may be configured such that there are more than one sensor mounting location along the fluid flow pathway of the coreflood apparatus. In some instances, the housing of the coreflood apparatus may be configured such that there is a sensor mounting location within a partition. In some instances, the housing of the coreflood apparatus may be configured such that there is a sensor mounting location proximate to the fluid inlet. In some instances, the housing of the coreflood apparatus may be configured such that there is a sensor mounting location proximate to the fluid outlet.

In FIG. 1A, an inlet sensor mounting location 181 is positioned upstream of inlet chamber 120A. A middle sensor mounting location 185 is positioned between chambers. For example, two middle sensor mounting locations are shown in FIG. 1A: between inlet chamber 120A and middle chamber 120B, and between middle chamber 120B and outlet chamber 120C. An outlet sensor mounting location 187 is positioned downstream of outlet chamber 120C.

In FIG. 1A, bifurcation line 10 defines a cross-sectional view from upstream to downstream, to be described. FIGS. 1B-1E show different examples of cross-sectional geometries of a partition gap 122B that may be formed along bifurcation line 10, according to embodiments of the present disclosure.

Figure 1B:
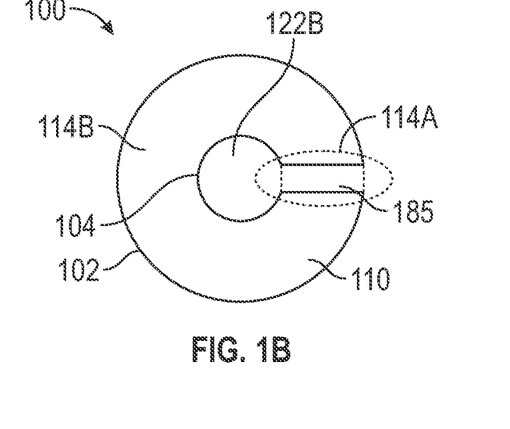
FIG. 1B shows a cutaway cross-sectional view of a coreflood apparatus, according to one or more embodiments.

FIG. 1B depicts a cross-sectional view of a coreflood apparatus 100 according to one or more embodiments based upon bifurcation line 10 of FIG. 1A. In FIG. 1B, the housing 110, the outer surface 102, the inner surface 104 define a thick circle-like shape as the partition and a small circle as partition gap 122B. A portion of the partition with sensor mounting location 114A interfaces the partition gap 122B. The middle sensor mounting location 185 defined by the portion of the partition with sensor mounting location 114A provides fluid communication with the fluid that would flow through partition gap 122B. The remainder of the partition is not associated with defining a sensor mounting location, so is demarcated as a portion of the partition without sensor mounting location 114B. The portion of the partition without sensor mounting location 114B may be formed of the same material as the rest of the housing 110.

Figure 1C:
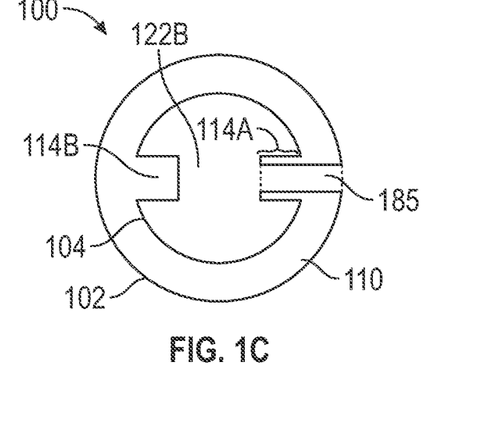
FIG. 1C shows a cutaway cross-sectional view of a coreflood apparatus, according to one or more embodiments.

FIG. 1C depicts a cross-sectional view of the coreflood apparatus 100 according to one or more other embodiments based upon bifurcation line 10 of FIG. 1A. In FIG. 1C, the housing 110, the outer surface 102, and the inner surface 104 define a thin circle-like shape as the partition and a large circle as partition gap 122B. A portion of the partition with sensor mounting location 114A protrudes into the partition gap 122B. The middle sensor mounting location 185 defined by the portion of the partition with sensor mounting location 114A provides fluid communication with the fluid that would flow through partition gap 122B. A second portion of the partition protrudes into the partition gap 122B. However, this second portion of the partition is not associated with defining a sensor mounting location, so is demarcated as a portion of the partition without sensor mounting location 114B.

Figure 1D:
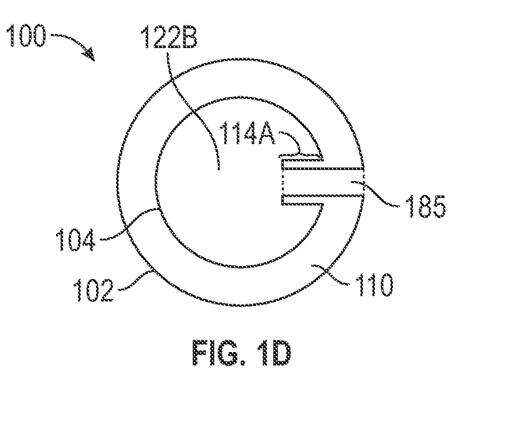
FIG. 1D shows a cutaway cross-sectional view of a coreflood apparatus, according to one or more embodiments.

FIG. 1D depicts a cross-sectional view of a coreflood apparatus 100 according to one or more other embodiments based upon bifurcation line 10 of FIG. 1A. In FIG. 1D, the housing 110, the outer surface 102, and the inner surface 104 define a thin circle-like shape as the partition and a large circle as partition gap 122B. The portion of the partition with sensor mounting location 114A protrudes into the partition gap 122B. The middle sensor mounting location 185 defined by the portion of the partition with sensor mounting location 114A provides fluid communication with the fluid that would flow through partition gap 122B. FIG. 1D is different from FIG. 1A in that the partition defines the middle sensor mounting location. That is, in FIG. 1D a portion of the partition without the sensor mounting location 114B is absent.

Figure 1E:
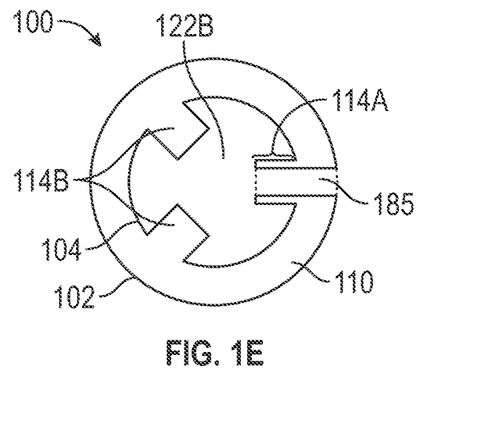
FIG. 1E shows a cutaway cross-sectional view of a coreflood apparatus, according to one or more embodiments.

FIG. 1E depicts a cross-sectional view of the coreflood apparatus 100 according to one or more other embodiments based upon bifurcation line 10 of FIG. 1A. In FIG. 1E, the housing 110, the outer surface 102, and the inner surface 104 define a thin circle-like shape as the partition and a large circle as partition gap 122B. The portion of the partition with sensor mounting location 114A protrudes into the partition gap 122B. The middle sensor mounting location 185 defined by the portion of the partition with sensor mounting location 114A provides fluid communication with the fluid that would flow through partition gap 122B. FIG. 1E is different from FIG. 1A in that there are two partitions that do not define the middle sensor mounting location. That is, there are two partitions (portion of partition without sensor mounting location 114B) that protrude into partition gap 122B.

In one or more embodiments, a coreflood apparatus is provided that includes a housing, such as a coreholder, with an inlet and an outlet and a partition therebetween. The partition separates the housing into separate chambers. The chambers are positioned in series and are configured to retain porous media, such as a core sample. A partition is also configured to retain porous media and to separate a sample of porous media from another sample. The partition or the housing itself may be configured to retain a sensor. The chambers and the partitions are configured such that when a core sample is present in the coreflood apparatus the introduced fluid traverses the core sample.

The housing of the apparatus includes walls that may define an inner surface and an outer surface of the housing. The housing may be configured to allow a fluid to traverse the interior of the housing. The inner surface of the housing defines the open space, or void, within the housing, including, but not limited to, an inlet, an outlet, a plurality of chambers, and at least one partition gap. There may be more than one inlet, such as a water inlet (to introduce aqueous solutions) and an oil inlet (to introduce oleaginous solutions). When the housing includes more than one inlet, the location of the more than one inlet is next to each other or just below the inlet in a parallel position (such as an inlet shown in the figures). In one or more embodiments, the housing is configured to retain porous media. When the porous media is a core sample, the housing may be called a coreholder.

The walls of the housing may be a suitable thickness that allows porous media retention and fluid flow according to one or more embodiments. The wall thickness of the housing depends on, for example, pressure rating and pipe size, and the wall thickness may be from about 0.1 inch (0.25 centimeter (cm)) to about 1 inch (2.5 cm), such as from about 0.343 inch (0.87 cm) to about 0.531 inch (1.35 cm). The walls of the housing may be a corrosion resistant material that is an alloy, such as a corrosion resistant nickel alloy. A suitable example of a nickel alloy is one that includes chromium, iron, molybdenum, or a combination thereof, for example, Hastelloy® (Haynes International; Kokomo, Indiana, USA). The housing may be configured to withstand a fluid pressure of up to 4,500 pounds per square inch (psi) (31 megapascal, MPa) and a temperature of up to 250° F. (121° C.).

In one or more embodiments, the coreflood apparatus includes a plurality of chambers, including, but not limited to, two chambers or more than two chambers. The coreflood apparatus may include two or more chambers, such as three or more, four or more, or five or more chambers. The chambers are positioned within the housing between the inlet and the outlet. A chamber is defined by an interior "open" space within the housing, where a chamber is separated from an adjacent chamber by a partition. A partition creates a "partition" space (gap or void) that separates two chambers; however, there is fluid connectivity between the two separate chambers. The gap or void between adjacent chambers defined by the partition may be called a partition gap. When a chamber is coupled to an inlet, it may be called an inlet chamber. When a chamber is coupled to an outlet, it may be called an outlet chamber. When a chamber is between an inlet chamber and an outlet chamber, it may be called a middle chamber.

When two middle chambers are included, they may be referred to as upstream middle chamber and downstream middle chamber. When more than two middle chambers are included, the upstream-most chamber may be referred to as the first middle chamber, labelled in series (second, third, and so on) to the final middle chamber (which would be the downstream-most middle chamber).

In one or more embodiments, the chambers are configured to retain porous media. For example, when the porous media is a core sample, a chamber retains the core sample. In one or more embodiments, the chambers are fluidly connected in series along a fluid flow pathway through the coreflood apparatus. The chambers are configured to prevent fluid bypass around the core sample contained within. For example, a core sample diameter may be substantially the same as an inner diameter of the chamber in which the core sample is held.

The size of a chamber may vary from one chamber to another depending on a variety of features and design choices, such as the size and thickness of the housing, and size and thickness of the partition(s). In one example, the chamber may be configured to retain porous media of up to about 20 inches (about 51 centimeters) in length and up to about 1.5 inches (about 3.81 centimeters) in diameter. The chamber may include a sleeve, where the sleeve mimics the overburden pressure underground.

As described above, the coreflood apparatus may include more than one partition, such as two or more partitions, three or more partitions, or four or more partitions, positioned between two adjacent chambers, separating the chambers physically from one another and through space (partition gap). A partition may be coupled or connected to the housing, e.g., the partition may be affixed to the inner surface of the housing. In some embodiments, a partition may be integral with the housing walls. The partition extends inward from the inner surface of the housing.

A partition may be made from a corrosion resistant material that is an alloy, such as a nickel alloy. A suitable example of a nickel alloy is one that includes chromium, iron, molybdenum, or a combination thereof, for example, Hastelloy® (Haynes International; Kokomo, Indiana, USA).

The size of a partition may vary. The length of the partition, measured from the inner surface of the housing to the tip of the partition, may protrude into the partition gap up to about 3 inches (7.62 cm). For example, the length of the partition may be from 0.1 to 3 inches (0.25 to 7.62 cm), such as from about 0.1 to 2 inches (0.25 to 5.08 cm), 0.5 to 3 inches (1.27 cm to 7.62 cm), 1 to 3 inches (2.54 to 7.62 cm), and 1 to 2 inches (2.54 to 5.08 cm). The lower limit height of the partition may be about 0.1 inches, so long as the partition is configured to retain the porous media and define the dimensions of the chamber (along with the inner surface of the housing). The height of the partition may range from about 0.1 to 3 inches, such as from about 0.1 to 2 inches, 0.5 to 3 inches, 0.5 to 2 inches, 1 to 3 inches, or 1 to 2 inches. The width of the partition may be up to about 10 inches. The lower limit width of the partition may be about 0.1 inches, so long as the partition is configured to retain the porous media and define the dimensions of the chamber (along with the inner surface of the housing). For example, the width of the partition may be from 0.1 to 3 inches, such as from about 0.1 to 2 inches, 0.5 to 3 inches, 0.5 to 2 inches, 1 to 3 inches, or 1 to 2 inches.

Method of Using Coreflood Apparatus

Figure 4:
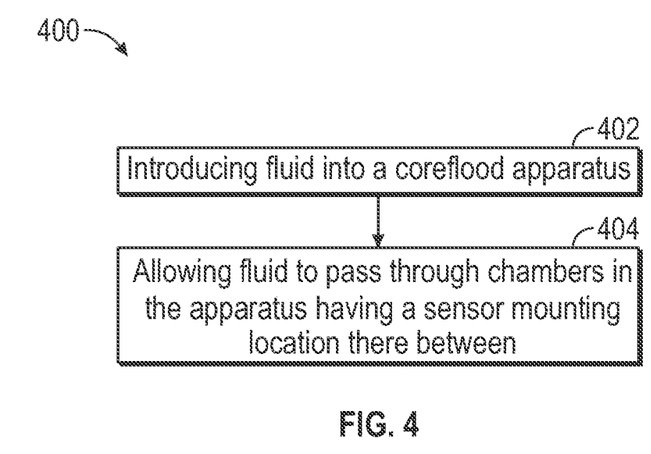
FIG. 4 shows elements of a method for introducing fluid into a coreflood apparatus, according to one or more embodiments.

FIG. 4 shows a method 400 according to one or more embodiments. The method 400 includes introducing fluid into a coreflood apparatus 402 and allowing fluid to pass through chambers in the coreflood apparatus 404, where the system includes a sensor mounting location between the chambers.

A method is provided that includes operating the system such that a fluid is introduced into the coreflood apparatus. The method of one or more embodiments may include operating the apparatus such that fluid passes through the chambers and partition gaps of the coreflood apparatus and contacts a sensor mounting location. In some embodiments, the system may be operated such that the fluid flow within the coreflood system may be dynamic, such as by adjusting the composition, flow rate, pressure, or temperature of the introduced fluid.

The method may include introducing a porous media into one or more chamber. In one or more embodiments, the method may include introducing fluid into the coreflood apparatus at an inlet and allowing the fluid to pass from the inlet to a sensor mounting location. The method may include allowing the fluid to pass through porous media, to multiple sensor mounting locations, and to the outlet.

In one or more embodiments, the method includes adjusting a flow rate, a pressure, or a temperature of the fluid. Such fluid adjustments occur at or upstream of the inlet. The flow rate of the fluid may be in a range of from about 0.5 to about 5 centimeters cubed per minute ($cm^3$/min). The fluid pressure may be in a range up to an overburden pressure of from about 450 pounds per square inch (psi) (about 3.1 MPa) to about 2500 psi (about 17.2 MPa). The coreflood system may withstand a back pressure in the range of from about 200 psi (about 1.3 MPa) to about 500 psi (about 3.5 MPa). A fluid pressure may be from about 3,000 psi (about 20.6 MPa) to about 3,500 psi (24.1 MPa). A fluid temperature may be from about room temperature, about 77°F. (about 25°C.), to about 250°F. (about 121°C.). The fluid pH may be any pH, for example, from 0 pH to 14 pH. In some embodiments, the fluid may be a brine having a salinity with a total dissolved solids content of greater than 200,000 ppm.

The method of one or more embodiments may continue for up to a month. For example, at a low flow rate such as from about 0.1 $cm^3$/min to about 4 $cm^3$/min, the experiment can be run for a time period of up to 1 month, such as from 3 days to a month, from 3 days to 4 weeks, from 3 days to 3 weeks, from 3 days to 2 weeks, or from 3 days to 1 week.

Coreflood System Including pH Sensors

Figure 2:
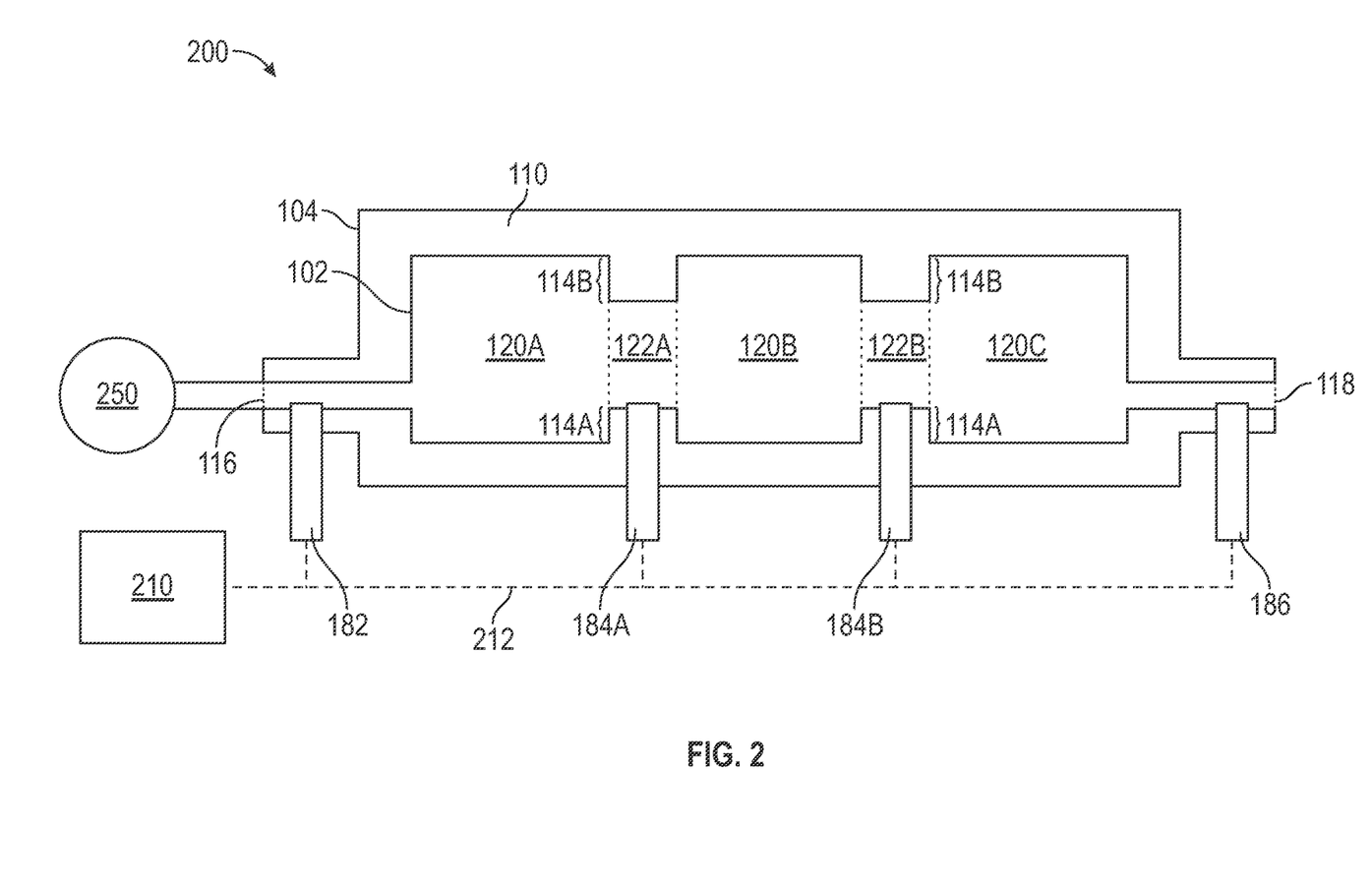
FIG. 2 shows a coreflood system with pH sensors, according to one or more embodiments.

FIG. 2 shows a coreflood system 200 according to one or more embodiments. The coreflood system 200 includes a coreflood apparatus of one or more embodiments. The coreflood system also includes several pH sensors, where a pH sensor is coupled to the coreflood apparatus at a sensor mounting location (in FIG. 2, each sensor is positioned within a sensor mounting location). FIG. 2 shows an inlet pH sensor 182, a middle pH sensor (two are shown in FIG. 2, upstream middle pH sensor 184A and downstream middle pH sensor 184B), and an outlet pH sensor 186. Each pH sensor is configured to contact the fluid contained within the housing 110 and to detect hydrogen ions in the fluid. For example, the inlet pH sensor 182 may detect hydrogen ions in the fluid at the inlet 116. The upstream middle pH sensor 184A may detect hydrogen ions in the fluid in the partition gap 122A. The downstream middle pH sensor 184B may detect hydrogen ions in the fluid in the partition gap 122B. The outlet pH sensor 186 may detect hydrogen ions in the fluid in the outlet 118.

Each pH sensor is also in data communication (hydrogen ion data) with data processing device 210. Each pH sensor may be coupled to the data processing device either physically or wirelessly. For example, in FIG. 2, the pH sensors (182, 184A, 184B, and 186) are coupled to a data processing device 210 utilizing a data conduit 212 (dotted line). The data processing device is configured to receive a data signal (hydrogen ion data) and to determine hydrogen ion concentration and pH within the fluid.

The coreflood system 200 may include a pump 250. The pump shown in FIG. 2 is fluidly coupled or connected to the coreflood apparatus and positioned upstream of the inlet 116.

Figure 3:
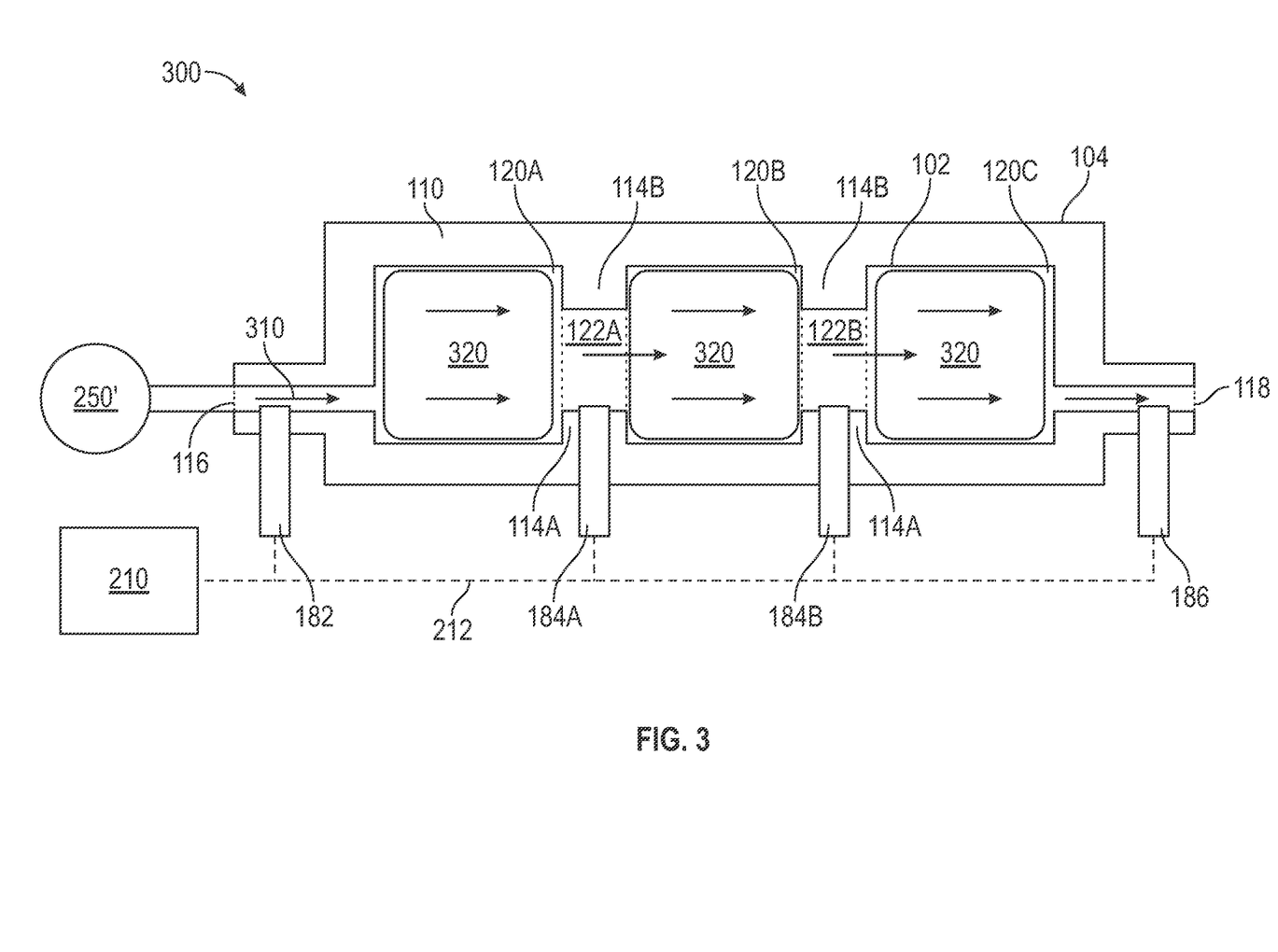
FIG. 3 shows a coreflood system in an active state including porous media and showing direction of fluid flow, according to one or more embodiments.

FIG. 3 shows a coreflood system 300 in an active state, according to one or more embodiments. Porous media 320 is shown in inlet chamber 120A, middle chamber 120B, and outlet chamber 120C. The pump 250' is in an active state, passing fluid to the inlet 116. Fluid 310 is flowing (arrows) through the coreflood system 300. The fluid 310 passes into inlet chamber 120A, middle chamber 120B, and outlet chamber 120C in succession and through the porous media 320 contained in the chambers. As shown in FIG. 3, fluid 310 may flow from the outlet 118 and out of the coreflood system 300 itself. Although not shown, a collection apparatus or vessel may be present downstream of the outlet 118 to collect the fluid 310.

In FIG. 3, the pH sensor(s) may detect hydrogen ions in the fluid in contact with the tip of the sensor(s). For example, in inlet 116 the inlet pH sensor 182 may detect the hydrogen ion concentration and pH of the fluid 310 just as it is introduced into the coreflood system. In partition gap 122A, the upstream middle pH sensor 184A may detect the hydrogen ion concertation of the fluid 310 just as it passes from the upstream core sample (porous media 320) in inlet chamber 120A. In partition gap 122B, the downstream middle pH sensor 184B may detect the hydrogen ion concertation of the fluid 310 just as it passes from the middle core sample (porous media 320) in middle chamber 120B. In outlet 118, the outlet pH sensor 186 may detect the hydrogen ion concertation of the fluid 310 just as it passes from the downstream core sample (porous media 320) in outlet chamber 120C and as it passes from the coreflood system. Each pH sensor is configured to communicate a signal associated with the hydrogen ions detected in the fluid as data to the data processing device 210. The data processing device 210 may determine hydrogen ion concentration and pH from the received data. The data processing device 210 may determine changes or differences in hydrogen ion concentration and pH at various positions along the fluid flow pathway of the coreflood apparatus.

In one or more embodiments, a coreflood system is provided that includes the coreflood apparatus, a pH sensor, and a data processing device. The coreflood system may include one or more pH sensors, such as two or more, or three or more pH sensors. A pH sensor is selective for detecting hydrogen ions in a fluid. The one or more sensors may be positioned anywhere along the fluid flow pathway within the housing, to be described. Multiple pH sensors may be positioned such that they contact the fluid along the fluid flow pathway within the housing of the coreflood apparatus. In this way, the coreflood system is configured to detect hydrogen ions with the pH sensors and to determine hydrogen ion concentration and pH with the data processing device.

When a plurality of pH sensors are included in a coreflood system of one or more embodiments, they may be positioned in series along a given fluid flow pathway. pH sensors positioned in series allow hydrogen ion data to be detected at different positions in a coreflood system, such as at an inlet, between chambers, and at an outlet.

In some instances, a pH sensor may be included at a sensor mounting location. In other instances, there may be less pH sensors than the total number of sensor mounting locations. As a non-limiting example, there may be two pH sensors and four sensor mounting locations.

An inlet pH sensor may be positioned in a sensor mounting location within the housing upstream of the chambers. An inlet pH sensor may be positioned in a fluid line upstream of the housing. There may be more than one inlet pH sensor.

An outlet pH sensor may be positioned within the housing downstream of the chambers. An outlet pH sensor may be positioned in an effluent line downstream of the housing. There may be more than one outlet pH sensor.

A middle pH sensor may be positioned at a location between two chambers. There may be one or more middle pH sensors.

A pH sensor includes a hydrogen ion detector portion. The detector portion is configured to be in fluid communication with fluid. The pH sensor is configured to detect hydrogen ions within the fluid. For example, as fluid passes over a pH sensor at the detector potion, the detector portion intermingles with hydrogen ions and transmits the response into a data signal (hydrogen ion data). The pH sensor may detect hydrogen ions continuously, intermittently, in a pulse-width manner, or a combination thereof.

The type of pH sensor is not particularly limited. Suitable examples of a pH sensor include, but are not limited to, high-temperature and high-pressure pH sensors. Meaning, the pH sensor may withstand a high-temperature and high-pressure condition. As used herein, "high-temperature and high-pressure" means a temperature of up to about 650°F. (343° C.) and a pressure of up to about 40,000 pounds per square inch (psi) (276 megapascals (MPa)). The pH sensor may be made from a material that is corrosion resistant or corrosion proof, such as 316 stainless steel, corrosion resistant nickel alloy (such as Hastelloy®), titanium, or a combination thereof. The pH sensor electrode (electrical conductor, etc.) is housed in the pH sensor. The pH sensor electrode or the pH sensor may have a protective covering, coating, or seal to withstand high-temperature, as would be appreciated by one of ordinary skill in the art. For example, the material Queon™ (Corr Instruments; Carson City, Nevada, USA) may provide sealability not limited to electrically insulating a pH sensor electrode at high-temperature and high-pressure.

Examples of pH sensors include a ZEUS™ pH sensor available from Advanced Sensor Technologies, Inc. (ASTI) (Torrance, California, USA) and a UltraDeg® High-Temperature and High-Pressure pH Electrode available from Con Instruments (Carson City, Nevada, USA). A reference solution may be used with a pH sensor of one or more embodiments. For example, a reference solution for calibration purposes may be added before a coreflooding experiment as would be appreciated by one of ordinary skill in the art.

The pH sensor may have a sensitivity depending on the temperature. For example, the sensitivity of the pH sensor may vary by up to 0.1 pH unit at two different temperatures.

The pH sensor may detect pH even in a high salinity fluid, such as a brine with a total dissolved solids (TDS) content of greater than 200,000 parts-per-million (ppm).

The pH sensor may be configured to detect hydrogen ions in presence of organic media, such as organic solvent, oil, or other organic material. For example, the pH sensor may detect hydrogen ions (pH) when the organic content of the aqueous solution is about 50 vol% (percent by volume) or less, such as up to 50 vol% organic media compared to the total volume of the fluid. A high concentration of organic media, such as about 50 vol% organic media compared to the total volume of the fluid, may age the pH sensor to an extent that the detection limit of the sensor is reduced compared to without a high concentration of organic media.

The pump (e.g., 250 in FIG. 2) may have a variable flow rate, or a variable pressure, or both a variable flow rate and pressure. The pump flow rate may be a rate between from about 0.5 to about 5 cubic centimeters per minute ($cm^3$/min) (or milliliters per minute, mL/min). The pump may withstand acid or base corrosion and high-temperature and high-pressure conditions.

A data processing device is configured to receive a data signal (hydrogen ion data) from a pH sensor and to determine hydrogen ion concentration and pH of a fluid. The data processing device may also determine a change in hydrogen ion concentration and pH of a fluid over time. The data processing device may include a computer processor. The data processing device may include a form of data processing with or without a computer processor, such as a potentiometer, an amperage meter, a voltage meter, a resistance meter, a multimeter, or other suitable form of data processing. The data processing device may include a receiver, including, but not limited to, a Wi-Fi, Bluetooth, or radio receiver.

Examples of porous media that may be used in a coreflood apparatus according to embodiments of the present disclosure may include, but is not limited to, an outcrop plug, a sand pack, a reservoir rock, or a combination thereof. The porous media may be a source of hydrogen ions. The porous media may be a single core sample that is cut into pieces, or multiple different core samples. Porous media is positioned in series along a given fluid flow pathway within a series of chambers of the coreflood apparatus or coreflood system. FIG. 3 shows an example with three samples of porous media positioned in series along a given fluid flow pathway.

The fluid may be an aqueous-based fluid. For example, the aqueous base of the fluid may include, but is not limited to, brine, seawater, freshwater, processed water, distilled water, alkaline water, reservoir water, a combination thereof, or other suitable types of water.

The fluid may be a source of hydrogen ions, meaning the fluid may include hydrogen ions (such as acids or salts that include hydrogen ions). A fluid without hydrogen ions may be used. Multiple types of fluid (fluids having different compositions) may be introduced, either simultaneously, one after the other, or intermittently. Generally, water and saline water, petroleum, oil, and formation water may be used, and mixtures thereof. Gas or alternating a gas and a liquid may also be used, such as occurs in mimicking $CO_2$ enhanced oil recovery processes.

The aqueous base fluid may include up to 50 volume % (vol%) organic media. Organic media may include solvent, hydrocarbon, microorganisms, or intractable organic material.

One of ordinary skill in the art would appreciate variations of a coreflood apparatus and a coreflood system. For example, the coreflood apparatus or system may include an overpressure burst disk and a relief valve to protect the system against accidental over-pressure. The relief valve may be located in the housing. A syringe pump may be used to control the injection pressure or flow rate setting. A heating system may include a heating element or heating tape around the apparatus, or the apparatus may be kept inside an industrial oven for heating.

Method of Using Coreflood System

Figure 5:
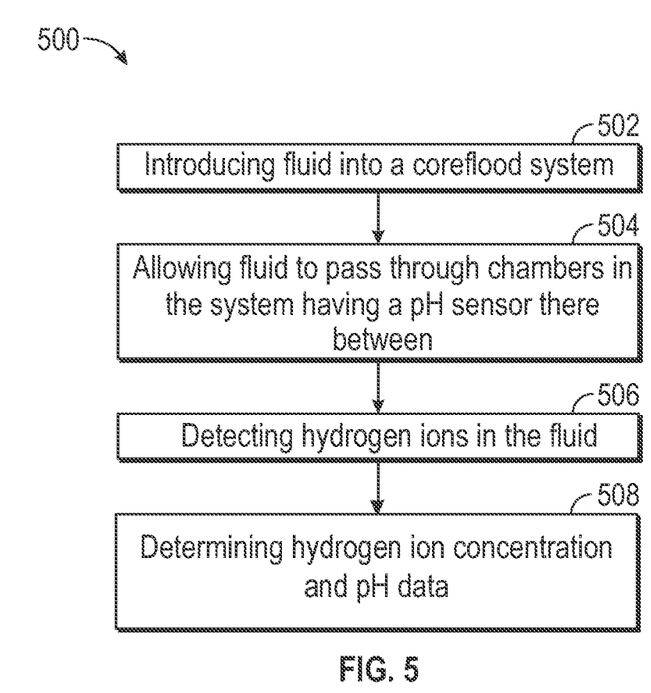
FIG. 5 shows elements of a method for determining pH in a fluid that is introduced into a coreflood system, according to one or more embodiments.

FIG. 5 shows a method 500 according to one or more embodiments. The method 500 shows introducing fluid into a coreflood system 502 and allowing fluid to pass through chambers in the coreflood system 504, where the system includes a pH sensor between the chambers. The method 500 includes detecting hydrogen ions 506 in the fluid and determining hydrogen ion concentration and pH data 508.

A method is provided that includes operating the system such that a fluid is introduced into the coreflood system, such as into the coreflood apparatus. The method may include operating the system such that hydrogen ion data is detected in the fluid flowing through the coreflood system, such as in portions of the coreflood apparatus. The method of one or more embodiments may include detection of hydrogen ions at one or more positions along the coreflood system, such as in portions of the coreflood apparatus. The method may include operating the system such that the hydrogen ion concentration and pH, or the change in hydrogen ion concentration and change in pH of the fluid within the coreflood system is determined, such as by using a data processing device. In some embodiments, the system may be operated such that the fluid flow within the coreflood system may be dynamic, such as by adjusting the composition, flow rate, pressure, or temperature of the introduced fluid.

The method may include introducing porous media into one or more chamber. In one or more embodiments, the method includes introducing fluid into the coreflood system at an inlet, after installing the porous media into the chamber(s), and directing the fluid from the inlet to a pH sensor. The method may include the fluid passing through porous media, interacting with multiple pH sensors, and passing from the outlet.

In one or more embodiments, the method includes detecting hydrogen ions in the fluid with a pH sensor. The method may include detecting hydrogen ions instantaneously, intermittently, or continuously over a period.

Hydrogen ions may be detected at different pH sensors positioned in the coreflood system. For example, hydrogen ions may be detected in the coreflood system at the inlet, the middle, the outlet, or at a combination thereof.

For example, the method may include detecting hydrogen ions at an inlet pH sensor as fluid is introduced into the coreflood system. As fluid passes through the chambers, the method may include detecting hydrogen ions at a middle pH sensor (and so on, where the coreflood system includes multiple middle pH sensors). As fluid passes from the outlet chamber, the method may include detecting hydrogen ions at an outlet pH sensor. Once the data processing device receives the hydrogen ion data, the method includes determining a hydrogen ion concentration and pH. The method may include determining a hydrogen ion concentration at two or more positions, such as the inlet, the middle, and the outlet. The method may include determining a pH at two or more positions, such as the inlet, the middle, and the outlet. The method may include determining a change in hydrogen ion concentration (or pH) at one or more position, such as a cumulative change in hydrogen ion concentration (or pH) at a position in the coreflood system (in coreflood apparatus).

In one or more embodiments, the method may include adjusting a flow rate, a pressure, or a temperature of the fluid. Generally, such fluid adjustments occur at or upstream of the inlet. The flow rate of the fluid may be in a range of from about 0.5 to about 5 $cm^3$/min. The fluid pressure may be in a range up to an overburden pressure of from about 450 pounds per square inch (psi) to about 2500 psi. The coreflood system may withstand a back pressure in the range of from about 200 psi to about 500 psi. A fluid pressure (pore pressure) may be from about 3,000 psia to about 3,500 psia. A fluid temperature may be from about room temperature (about 77° F.) (about 25° C.) to about 250° F. (about 121° C.).

The method of one or more embodiments may continue for up to a month. For example, at a low flow rate such as from about 0.01 $cm^3$/min to about 1 $cm^3$/min, the experiment can be run for a time period of up to 1 month, such as from 3 days to a month, from 3 days to 4 weeks, from 3 days to 3 weeks, from 3 days to 2 weeks, or from 3 days to 1 week.

Advantages

One or more embodiments of the coreflood system and method of use allows hydrogen ion detection in-situ. Meaning, hydrogen ion concentration and pH data is collected internally within a 'closed' system (within the housing). Internal and in-situ hydrogen ion detection may provide insight into reaction mechanisms and properties of fluid specific to instantaneous through-core hydrogen ion measurements.

For example, fluid chemistry may behave differently within a porous media, or between two different porous media because of different wetting conditions and rock minerology. It is believed that such measurements advantageously imitate fluid flow within reservoir, such as internal flow between and hydrogen ion concentration or pH variation between porous media. Such measurements will help to understand the in-situ interactions between fluids and rock minerals.

In addition, the ability to analyze hydrogen ion data from within a 'closed' system prevents artifacts and impurities from being collected, leading to more accurate results. For example, detecting hydrogen ions of the fluid in-situ provides accurate results compared to collecting effluent fractions. For example, the coreflood system of one or more embodiments may be controlled such that $CO_2$ in the air does not dissolve into the fluid. Preventing $CO_2$ dissolution advantageously provides stable hydrogen ion data and accurate hydrogen ion concentration and pH results, as compared to, for example, collecting effluent fractions outside of a coreflooding apparatus.

As well, analyzing the hydrogen ions of the fluid in-situ may allow for measurements at various temperatures and pressures. In this way, the interaction between injected fluid, rock, minerals, and native fluid (for example, reservoir fluid in the rock or mineral) at high-temperature and high-pressure may be studied, for example, without exposure to air at atmosphere.

The coreflood system of one or more embodiments includes chambers in series. This allows for increased fluid exposure to porous media, depending on the length of the chambers, compared to a coreflood system that may include chambers in parallel.

Advantageously, in-situ detection of hydrogen ion data removes an extent of operator skill and labor time as compared to a conventional method, for example, effluent collection and analysis. The system and method of one or more embodiments overcomes uncertainties in determining hydrogen ion concentration and pH to provide robust, reliable, and accurate measurements.

Different core samples may be included in one or more embodiments to detect pH changes from one core to the next. For example, one core may be oil-wet and another core may be water-wet, and variations thereof and between oil-wet and water-wet. The apparatus, system, and method of one or more embodiments also allows pH measurement 'between' a core sample (such as a cut core sample where the core itself may have an average porosity of about 20% with pore sizes in the micrometer range).

As a result, applying one or more embodiments of the method herein may accurately predict a water flooding process, providing advantageous data to optimize water-flooding in the field and increase oil recovery.

As used here and in the appended claims, the words "comprise," "has," and "include" and all grammatical variations thereof are each intended to have an open, non-limiting meaning that does not exclude additional elements or steps.

When the word "about" is used, this term may mean that there can be a variance in value of up to ±10%, up to ±5%, up to ±2%, up to ±1%, up to ±0.5%, up to ±0.1%, up to ±0.01%, up to +10%, up to +5%, up to +2%, up to +1%, up to +0.5%, up to +0.1%, up to +0.01%, up to -10%, up to -5%, up to -2%, up to -1%, up to -0.5%, up to -0.1%, or up to -0.01%.

Ranges may be expressed as from about one particular value to about another particular value, inclusive. When such a range is expressed, it should be understood that another one or more embodiments is from the one particular value to the other particular value, along with all particular values and combinations thereof within the range.

While one or more embodiments of the present disclosure have been described with respect to a limited number of embodiments, those skilled in the art, having benefit of this disclosure, will appreciate that other embodiments can be devised, which do not depart from the scope of the disclosure. Accordingly, the scope of the disclosure should be limited only by the attached claims.

What is claimed:

1. A coreflood system, comprising:
    a housing including an inlet end and an outlet end;
    an inlet positioned at the inlet end;
    an outlet positioned at the outlet end;
    two chambers positioned within the housing between the inlet and the outlet, configured to retain porous media, where the two chambers are in series along a fluid flow pathway through the coreflood system;
    a partition extending from an inner surface of the housing and positioned between the inlet and the outlet;
    a pH sensor provided in a sensor mounting location in the housing,
        where the pH sensor has access to the fluid flow pathway.

2. The coreflood system of claim 1, further comprising a data processing device in communication with the pH sensor.

3. The coreflood system of claim 1, wherein the pH sensor and the sensor mounting location are provided in the partition.

4. The coreflood system of claim 1, where the sensor mounting location includes an inlet sensor mounting location, positioned upstream of the two chambers, and where the pH sensor includes an inlet pH sensor coupled to the inlet sensor mounting location.

5. The coreflood system of claim 1, where the sensor mounting location includes a middle sensor mounting location, positioned between the two chambers, and where the pH sensor includes a middle pH sensor coupled to the middle sensor mounting location.

6. The coreflood system of claim 1, where the sensor mounting location includes an outlet sensor mounting location, positioned downstream of the two chambers, and where the pH sensor includes an outlet pH sensor coupled to the outlet sensor mounting location.

7. The coreflood system of claim 1, where the pH sensor is made from one or more selected from the group consisting of 316 stainless steel, corrosion resistant nickel alloy, and titanium.

8. The coreflood system of claim 1, further comprising at least one additional chamber positioned in the housing and in series along the fluid flow pathway.

9. The coreflood system of claim 1, wherein the partition is integrally formed with the housing.

10. The coreflood system of claim 1, further comprising a pump fluidly connected to the inlet.

11. A method, comprising:
    providing a coreflood system comprising:
        a housing including an inlet end and an outlet end, where the inlet is positioned at the inlet end;
        an outlet positioned at the outlet end;
        two chambers positioned within the housing between the inlet and the outlet,
            where the two chambers are in series along a fluid flow pathway through the coreflood system;
        a partition extending from an inner surface of the housing and positioned between the two chambers; and
        a pH sensor coupled to a sensor mounting location in the housing, wherein the pH sensor has access to the fluid flow pathway;
    providing a porous medium in the two chambers;
    directing a fluid through the coreflood system, from the inlet through the fluid flow pathway;
    using a data processing device coupled to the pH sensor to collect hydrogen ion data from the pH sensor and determine a hydrogen ion concentration and pH within the fluid.

12. The method of claim 11, further comprising determining a change in the hydrogen ion concentration and pH in the fluid with the data processing device, using the hydrogen ion data from the pH sensor.

13. The method of claim 11, where the porous media is a core sample.

14. The method of claim 13, where the core sample is an outcrop plug, a sand pack, a reservoir rock, or a combination thereof.

15. The method of claim 11, where the fluid includes 50 vol% organic media compared to total volume of the fluid.

16. The method of claim 11, where the fluid comprises brine, saline, water, formation water, or a combination thereof.

17. The method of claim 11, further comprising adjusting a flow rate of the fluid in a range of from about 0.5 to about 5 cubic centimeters per minute.

18. The method of claim 11, further comprising adjusting fluid temperature and pressure in a high-temperature and high-pressure range a range up to about 40,000 psi (276 MPa) and 650° F. (343° C.).

19. The method of claim 11, where introducing the fluid occurs for a time period of up to 1 month.

\* \* \* \* \*

UNITED STATES PATENT AND TRADEMARK OFFICE
CERTIFICATE OF CORRECTION

PATENT NO. : 11,692,990 B1
APPLICATION NO. : 17/648833
DATED : July 4, 2023
INVENTOR(S) : Mohammed Badri Al-Otaibi et al.

It is certified that error appears in the above-identified patent and that said Letters Patent is hereby corrected as shown below:

On the Title Page

Item (72), the Inventors "Mohammed Badri Al-Otaibi, Dhahran (SA); Dong Kyu Cha, Dhahran (SA)" should read -- Mohammed Badri Al-Otaibi, Dhahran (SA); Dong Kyu Cha, Dhahran (SA); Hassan Sakar Alqahtani, Dhahran (SA) --

Signed and Sealed this
Ninth Day of July, 2024

Katherine Kelly Vidal
*Director of the United States Patent and Trademark Office*